(12) United States Patent
Brichta

(10) Patent No.: US 12,336,997 B2
(45) Date of Patent: Jun. 24, 2025

(54) COMPOSITIONS AND METHODS FOR TREATING VASCULAR ANOMALIES, NEVUS SEBACEOUS SYNDROME, EPIDERMAL NEVI, AND NEUROFIBROMAS

(71) Applicant: Chemistry RX, Folcraft, PA (US)

(72) Inventor: Lars Brichta, Brooklyn, NY (US)

(73) Assignee: Chemistry RX, Folcraft, PA (US)

( * ) Notice: Subject to any disclaimer, the term of this patent is extended or adjusted under 35 U.S.C. 154(b) by 0 days.

(21) Appl. No.: 18/333,375

(22) Filed: Jun. 12, 2023

(65) Prior Publication Data

US 2023/0330092 A1    Oct. 19, 2023

Related U.S. Application Data

(63) Continuation of application No. 16/949,264, filed on Oct. 22, 2020, now abandoned.

(60) Provisional application No. 62/924,202, filed on Oct. 22, 2019.

(51) Int. Cl.
| | |
|---|---|
| *A61K 9/06* | (2006.01) |
| *A61K 9/127* | (2006.01) |
| *A61K 31/519* | (2006.01) |
| *A61K 47/20* | (2006.01) |
| *A61P 17/00* | (2006.01) |

(52) U.S. Cl.
CPC .............. *A61K 31/519* (2013.01); *A61K 9/06* (2013.01); *A61K 9/127* (2013.01); *A61K 47/20* (2013.01); *A61P 17/00* (2018.01)

(58) Field of Classification Search
None
See application file for complete search history.

(56) References Cited

U.S. PATENT DOCUMENTS

| | | | |
|---|---|---|---|
| 2019/0105261 A1* | 4/2019 | Waugh | A61K 31/573 |
| 2020/0024666 A1* | 1/2020 | Greene | A61P 9/00 |
| 2021/0060018 A1* | 3/2021 | Zhang | A61P 17/06 |

OTHER PUBLICATIONS

Arora et al (International Journal of Clinical Pediatric Dentistry, 2014, 7(1), 43-46). (Year: 2014).*

* cited by examiner

*Primary Examiner* — Celeste A Roney

(74) *Attorney, Agent, or Firm* — FisherBroyles, LLP; Christy G. Rothwell

(57) ABSTRACT

Compositions and methods for treating congenital epidermal or dermal hyperplasia by using topically administered oncokinase inhibitors such as trametinib, pyrrole derivatives, TAK-733, CH4987655, RDEA119/BAY 869766, cobimetinib, binimetinib, selumetinib, and the like are described herein.

14 Claims, No Drawings

COMPOSITIONS AND METHODS FOR TREATING VASCULAR ANOMALIES, NEVUS SEBACEOUS SYNDROME, EPIDERMAL NEVI, AND NEUROFIBROMAS

CROSS-REFERENCE TO RELATED APPLICATIONS

This application is a continuation of U.S. application Ser. No. 16/949,264, filed Oct. 22, 2020, which claims priority to and benefit of U.S. Provisional No. 62/924,202 entitled "Methods For Treating Congenital Epidermal Hyperplasia And Compositions For Same" filed Oct. 22, 2019, the entire contents of which are hereby incorporated by reference in their entirety.

SUMMARY OF THE INVENTION

Various embodiments of the invention are directed to topical compositions including an oncokinase inhibitor, a solubility enhancer, and a base. In some embodiments, the oncokinase inhibitor may be trametinib (N-(3-{3-Cyclopropyl-5-[(2-fluoro-4-iodophenyl)amino]-6,8-dimethyl-2,4,7-trioxo-3,4,6,7-tetra hydropyrido[4,3-d]pyrimidin-1(2H)-yl}phenyl)acetamide), pyrrole derivatives, TAK-733 (one of a series of 8-methylpyrido[2,3-d]pyrimidine-4,7(3H,8H)-dione derivatives), CH4987655 and RDEA119/BAY 869766, cobimetinib ((S)-[3,4-Difluoro-2-(2-fluoro-4-iodophenylamino)phenyl][3-hydroxy-3-(piperidin-2-yl)azetidin-1-yl]methanone), binimetinib (5-((4-bromo-2-fluorophenyl)amino)-4-fluoro-N-(2-hydroxyethoxy)-1-methyl-1H-benzo[d]imidazole-6-carboxamide), selumetinib (6-(4-bromo-2-chloroanilino)-7-fluoro-N-(2-hydroxyelhoxy)-3-methylbenzimidazole-5carboxamide), PD-325901, Cl-1040, PD035901, tetrathiomolybtate, TAK-933, and the like and combinations thereof. The solubility enhancer of such embodiments may be ethyl acetate, ethanol, methanol, dimethylformamide (DMF), acetone, acetonitrile, tetrahydrofuran (THF), acetic acid, dimethyl sulfoxide (DMSO), chloroform, and the like and combinations thereof, and the base in such embodiments, may be white petrolatum, white petrolatum USP, mineral jelly, petroleum jelly, yellow petrolatum, yellow soft paraffin, white soft paraffin, fats, waxes, sterols, fat-soluble vitamins, monoglycerides, diglycerides, triglycerides, phospholipids, PCCA plasticized base, and and the like and combinations thereof. In some embodiments, the base may be a cream base, an emollient base, or a liposomal base. The compositions of various embodiments may be in the form of a topical liquids, creams, lotions, foams, or liniments.

Further embodiments are directed to methods for making a topical composition including the steps of dissolving an oncokinase inhibitor in a solubility enhancer or solvent to create a oncokinase inhibitor solution and combining the oncokinase inhibitor with a base. In some embodiments, the oncokinase inhibitor may be tramethinib (N-(3-{3-Cyclopropyl-5-[(2-fluoro-4-iodophenyl)amino]-6,8-dimethyl-2,4,7-trioxo-3,4,6,7-tetra hydropyrido[4,3-d]pyrimidin-1(2H)-yl}phenyl)acetamide), pyrrole derivatives, TAK-733 (one of a series of 8-methylpyrido[2,3-d]pyrimidine-4,7(3H,8H)-dione derivatives), CH4987655 and RDEA119/BAY 869766, cobimetinib ((S)[3,4-Difluoro-2-(2-fluoro-4-iodophenylamino)phenyl][3-hydroxy-3-(piperidin-2-yl)azetidin-1-yl]methanone), binimetinib (5-((4-bromo-2-fluorophenyl)amino)-4-fluoro-N-(2-hydroxyethoxy)-1-methyl-1H-benzo[d]imidzole-6-carboxamide), selumetinib (6-(4-bromo-2-chloroanilino)-7-fluoro-N-(2-hydroxyelhoxy)-3-methylbenzimidazole-5-carboxamide), PD-323901, Cl-1040, PD035901, tetrathiomolybtate, TAK-933, and the like and combinations thereof. The solubility enhancer of such embodiments may be ethyl acetate, ethanol, methanol, dimethylformamide (DMF), acetone, acetonitrile, tetrahydrofuran (THF), acetic acid, dimethyl sulfoxide (DMSO), chloroform, and the like and combinations thereof, and the base in such embodiments, may be white petrolatum, white petrolatum USP, mineral jelly, petroleum jelly, yellow petrolatum, yellow soft paraffin, white soft paraffin, fats, waxes, sterols, fat-soluble vitamins, monoglycerides, diglycerides, triglycerides, phospholipids, PCCA plasticized base, and and the like and combinations thereof. In some embodiments, the base may be a cream base, an emollient base, or a liposomal base. The compositions of various embodiments may be in the form of a topical liquids, creams, lotions, foams, or liniments.

Other embodiments are directed to methods for treating congenital epidermal, dermal hyperplasia, or vascular anomalies by administering to a patient in need of treatment a composition containing an oncokinase inhibitor, a solubility enhancer, and a base. In some embodiments, administering may include applying the composition to the skin of the patient, and in certain embodiments, the methods may include readministering the composition to the patient The patient of such embodiments may have, been diagnosed with, or exhibit symptoms of congenital epidermal hypetplasia, congenital dermal hyperplasia, Costello syndrome, nevus sebaceous syndrome, and the like or combinations thereof. In certain embodiments, the patient may have, been diagnosed with, or exhibit symptoms of port-wine stains, capillary malformations, Sturge-Weber syndrome, Klippel-Trenaunay syndrome, venous malformation, and lymphatic malformations. In some embodiments, the oncokinase inhibitor may be trametinib (N-(3-{3-Cyclopropyl-5-[(2-fluoro-4-iodophenyl)amino]-6,8-dimethyl-2,4,7-trioxo-3,4, 6,7-tetra hydropyrido[4,3-d]pyrimidin-1(2H-yl}phenyl)acetamide), pyrrole derivatives, TAK-733 (one of a series of 8-methlpyrido[2,3-d]pyrimidine-4,7(3H,8H)-dione derivatives), CH4987655 and RDEA119/BAY 869766, cobimetinib ((S)[3,4-Difluoro-2-(2-fluoro-4-iodophenylamino)phenyl][3-hydroxy-3-(piperidin-2-yl)azetidin-1-yl]methanone), binimetinib (5-((4-bromo-2-fluorophenyl)amino)-4-fluoro-N-(2-hydroxyethoxy)-1-methyl-1H-benzo[d]imidzole-6-carboxamide), selumetinib (6-(4-bromo-2-chloroanilino)-7-fluoro-N-(2-hydroxyelhoxy)-3-methylbenzimidazole-5-carboxamide), PD-325901, Cl-1040, PD035901, tetrathiomolybtate, TAK-933, and the like and combinations thereof. The solubility enhancer of such embodiments may be ethyl acetate, ethanol, methanol, dimethylformamide (DMF), acetone, acetonitrile, tetrahydrofuran (THF), acetic acid, dimethyl sulfoxide (DMSO), chloroform, and the like and combinations thereof, and the base in such embodiments, may be white petrolatum, white petrolatum USP, mineral jelly, petroleum jelly, yellow petrolatum, yellow soft paraffin, white soft paraffin, fats, waxes, sterols, fat-soluble vitamins, monoglycerides, diglycerides, triglycerides, phospholipids. PCCA plasticized base, and and the like and combinations thereof. In some embodiments, the base may be a cream base, an emollient base, or a liposomal base. The compositions of various embodiments may be in the form of a topical liquids, creams, lotions, foams, or liniments.

DETAILED DESCRIPTION

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art. Where a range of values is provided, it is intended that each intervening value between the upper and lower limit of that range and any other stated or intervening value in that stated range is encompassed within the disclosure. For example, if a range of 1 ml to 8 ml is stated, 2 ml, 3 ml, 4 ml, 5 ml, 6 ml, and 7 ml are also intended to be explicitly disclosed, as well as the range of values greater than or equal to 1 ml and the range of values less than or equal to 8 ml.

All percentages, parts and ratios are based upon the total weight of the topical compositions and all measurements made are at about 25° C., unless otherwise specified.

The singular forms "a," "an," and "the" include plural referents unless the context clearly dictates otherwise. Thus, for example, reference to a "polymer" includes a single polymer as well as two or more of the same or different polymers; reference to an "excipient" includes a single excipient as well as two or more of the same or different excipients, and the like.

The word "about" when immediately preceding a numerical value means a range of plus or minus 10% of that value, e.g., "about 50" means 45 to 55, "about 25,000" means 22,500 to 27,500, etc., unless the context of the disclosure indicates otherwise, or is inconsistent with such an interpretation. For example, in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

The terms "administer," "administering" or "administration" as used herein refer to either directly administering a compound (also referred to as an agent of interest) or pharmaceutically acceptable salt of the compound (agent of interest) or a composition to a subject.

The term "carrier" as used herein encompasses carriers, excipients, and diluents, meaning a material, composition, or vehicle, such as a liquid or solid filler, diluent, excipient, solvent or encapsulating material involved in carrying or transporting a pharmaceutical, cosmetic or other agent across a tissue layer such as the stratum corneum or stratum spinosum.

The term "disorder" is used in this disclosure to mean, and is used interchangeably with the terms disease, condition, or illness, unless otherwise indicated.

The terms "effective amount" and "therapeutically effective amount" are used interchangeably in this disclosure and refer to an amount of a compound that, when administered to a subject, is capable of reducing a symptom of a disorder in a subject or enhance, reduce, normalize, or adjust the growth, texture, appearance, color, sensation, or hydration of the intended tissue treatment area. The actual amount which comprises the "effective amount" or "therapeutically effective amount" will vary depending on a number of conditions including, but not limited to, the severity of the disorder, the size and health of the patient, and the route of administration. A skilled medical practitioner can readily determine the appropriate amount using methods known in the medical arts.

The phrase "pharmaceutically acceptable" or "cosmetically acceptable" is employed herein to refer to those agents of interest/compounds, salts, compositions, dosage forms, etc, which are—within the scope of sound medical judgment—suitable for use in contact with the tissues of human beings and/or other mammals without excessive toxicity, irritation, allergic response, or other problem or complication, commensurate with a reasonable benefit/risk ratio. In some aspects, pharmaceutically acceptable means approved by a regulatory agency of the federal or a state government or listed in the U.S. Pharmacopeia or other generally recognized pharmacopeia for use in mammals (e.g. animals), and more particularly, in humans.

The term "salts" as used herein embraces pharmaceutically acceptable salts commonly used to form alkali metal salts of free acids and to form addition salts of free bases. The nature of the salt is not critical, provided that it is pharmaceutically acceptable. The term "salts" also includes solvates of addition salts, such as hydrates, as well as polymorphs of addition salts. Suitable pharmaceutically acceptable acid addition salts can be prepared from an inorganic acid or from an organic acid. Non-limiting examples of such inorganic acids are hydrochloric, hydrobromic, hydroiodic, nitric, carbonic, sulfuric, and phosphoric acid. Appropriate organic acids can be selected from aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric and galacturonic acid.

The term "patient" and "subject" are interchangeable and may be taken to mean any living organism which may be treated with compounds of the present invention. As such, the terms "patient" and "subject" may include, but is not limited to, any non-human mammal, primate or human. In some embodiments, the "patient" or "subject" is a mammal, such as mice, rats, other rodents, rabbits, dogs, cats, swine, cattle, sheep, horses, primates, or humans. In some embodiments, the patient or subject is an adult, child or infant. In some embodiments, the patient or subject is an adult or child human.

The term "treating" is used herein, for instance, in reference to methods of treating a disorder or a condition, and generally includes the administration of a compound or composition which reduces the frequency of, or delays the onset of, symptoms of a medical condition or enhance, reduce, normalize or adjust the growth, texture, appearance, color, sensation, or hydration of the intended tissue treatment area of the tissue surface in a subject relative to a subject not receiving the compound or composition. This can include reversing, reducing, or arresting the symptoms, clinical signs, and underlying pathology of a condition in a manner to improve or stabilize a subject's condition. For example, in the context of a bacterial, microbial, fungal, or protozoal infection, "treating" refers to the reduction in bacterial, microbial, fungal, or protozoal load and/or improvement in symptoms related to the infection.

As used herein, the term "therapeutic" means an agent utilized to treat, combat, ameliorate, prevent or improve an unwanted condition or disease of a subject. In part, embodiments described herein may be directed to the treatment of various skin diseases, conditions, or disorders or symptoms thereof, including, but not limited to, benign proliferations, neoplasms, superficial blood vessel anomalies (tumors and malformations), epidermolysis bullosa, wounds and sores, Langerhans Cell Histiocytosis, Tuberous sclerosis, premalignancies, or malignancies of the skin, as well as the enrichment of immune cells in the skin. The skin condition may be a virally induced or non-virally induced cutaneous growth or proliferation. The skin condition may be an inflammatory condition. The skin condition may be a hyperproliferative condition. The skin condition may be a genetically-determined condition. The skin condition may be ageing including intrinsic and extrinsic changes (e.g., photoaging (ultraviolet light induced changes)), pigmentary changes, fine lines and rhytides. In some embodiments, the skin condition may be selected from Human Papilloma Virus induced lesions e.g., warts, common warts, palmoplantar warts, flat warts, recurrent warts, recalcitrant warts, treatment naïve warts, epidermodysplasia verruciformis related warts, anogenital warts, condyloma accuminatum, cervical dysplasias or neoplasias, e.g., cervical intraepithelial neoplasia (CIN); Herpesvirus related lesions including those induced by HHV-1 (HSV-1), HHV-2 (HSV-2), HHV-3 (varicella-zoster virus) e.g., chicken pox, Herpes zoster, shingles; Poxvirus induced lesions e.g., molluscum contagiosum, orf; callus, cutaneous horns, corns, acrochordons, fibroepithelial polyps, prurigo nodularis, actinic keratoses, squamous cell carcinoma, squamous cell carcinoma in situ, keratoacanthoma, basal cell carcinoma, cutaneous lymphomas and benign lymphocytic infiltrates & hyperplasias of the skin, clear cell acanthoma, large cell acanthoma, epidermolytic acanthoma, porokeratosis, hyperkeratosis, keratosis pilaris, lichenoid keratosis, acanthosis, acanthosis nigricans, confluent and reticulated papillomatosis, nevi, including e.g., dermal nevi, epidermal nevi, compound nevi, ILVEN (inflammatory linear verrucous epidermal nevi), nevus sebaceous, nevus comedonicus, and the like; acne, e.g., comedonal acne, inflammatory acne, papular acne, pustular acne, cystic acne; cysts, e.g., epidermoid cysts, milia, trichilemmal cysts, follicular cysts, proliferating cysts, dermoid cysts, pilonidal cysts, apocrine cysts, eccrine cysts, sebaceous cysts, mucous cysts, myxoid cysts, ganglion cysts, synovial cysts, vellus hair cysts, steatocystoma, hidrocystoma; adnexal neoplasms e.g., trichofolliculoma, fibrofolliculoma, perifollicular fibroma, trichodiscoma, nevus sebaceous, chondroid syringoma, trichoepithelioma, trichoblastoma, desmoplastic trichoepithelioma, pilomatricoma, pilomatrical carcinoma, tricholemmoma, trichelemmal carcinoma, tumor of the follicular infundibulum, tricoadenoma, proliferating pilar tumor, sebaceous hyperplasia, sebaceous adenoma, sebaceous epithelioma, sebaceous carcinoma, syringoma, poroma, hidradenoma, apocrine hidradenoma, spiradenoma, cylindroma, eccrine nevus (eccrine hamartoma), papillary adenoma, papillary adenocarcinoma; benign melanocytic proliferations or neoplasms e.g., ephilides, café-au-lait macules, Becker's melanosis, lentigines, solar lentigines, lentigo simplex, mucosal melanocytic lesions, Mongolian spots, Nevus of Ota, blue nevus, common acquired melanocytic nevi (nevocellular nevus, "moles"), congenital nevi, nevus spilus, recurrent nevi; vascular and perivascular neoplasms and reactive hyperplasias e.g., hemangiomas, cherry angiomas, hobnail hemangiomas (targeted hemosiderotic hemangiomas), tufted angiomas, hemangioendotheliomas, angiolymphoid hyperplasia with eosinophilia (ALHE), Glomus tumors (glomangiomas), hemangiopericytomas; cutaneous neural and neuroendocrine neoplasms e.g., neuromas, Schwannomas, neurofibromas, nerve sheath tumor, nerve sheath myxoma, neurothekeoma, granular cell tumor; fibrotic and fibrohistiocytic proliferations e.g., acrochordons, fibroepithelial polyps, fibromas, fibrous papules, angiofibromas, pearly penile papules, periungual fibromas, dermatofibromas, fibrokeratomas, sclerotic or pleomorphic fibromas, connective tissue nevi; cutaneous scars, hyperplasias, keloids, rosacea, cutaneous fungal, dermatophyte & mold infections, onychomycosis, hyperpigmentation, rhytides, psoriasis, malignant melanoma, seborrheic keratosis, seborrheic keratosis variants including e.g., dermatosis papulosis nigra, inverted follicular keratosis/keratoma warty dyskeratosis/warty dyskeratoma, acrokeratosis verruciformis, stucco keratosis; or a combination thereof.

By hereby reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by hereby reserving the right to proviso out or exclude any individual substituents, analogs, compounds, ligands, structures, or groups thereof, or any members of a claimed group, less than the full measure of this disclosure can be claimed for any reason. Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

Various embodiments are directed to topical compositions containing one or more oncokinase inhibitor, and methods for treating congenital epidermal or dermal hyperplasia by administering such topical compositions to a subject in need of treatment, and in some embodiments, the topical compositions may reduce hyperplasia, reduce discoloration associated with hyperplasia, and relief of symptoms associated with congenital epidermal or dermal hyperplasia. In particular embodiments, the topical compositions may be used to treat congenital epidermal or dermal hyperplasia such as Costello syndrome and nevus sebaceous syndrome. In further embodiments, the compositions may be used to treat vascular anomalies such as port-wine stains, capillary malformations that are flat, reddish lesions that darken with age, nevus simplex or vascular stain, and capillary malformations associated with Sturge-Weber syndrome and Klippel-Trenaunay syndrome, venous malformation, and lymphatic malformations. In some embodiments, the methods for treating vascular anomalies may include administering a topical composition containing an oncokinase inhibitor to a subject in need of treatment.

The oncokinse inhibitor of various embodiments may be any oncokinase inhibitor, and in some embodiments, the oncokinase inhibitor may be capable of inhibiting kinases associated with/that belong to the human RAS/RAF/MEK/ERK signaling cascade. In some embodiments, the oncokinase inhibitor may inhibit HRAS. Examples, of suitable oncokinse inhibitors include trametinib (N-(3-{3-Cyclopropyl-5-[(2-fluoro-4-iodophenyl)amino]-6,8-dimethyl-2,4,7-trioxo-3,4,6,7-tetra hydropyrido[4,3-d]pyrimidin-1(2H)-yl}phenyl)acetamide), pyrrole derivatives, TAK-733 (one of a series of 8-methylpyrido[2,3-d]pyrimidine-4,7(3H,8H)-dione derivatives), CH4987655 and RDEA119/BAY 869766, cobimetinib ((S)-[3,4-Difluoro-2-(2-fluoro-4-iodophenylamino)phenyl][3-hydroxy-3-(piperidin-2-yl)azetidin-1-yl]methanone), binimetinib (5-((4-bromo-2-fluorophenyl)amino)-4-fluoro-N-(2-hydroxyethoxy)-1-methyl-1H-benzo[d]imidzole-6-carboxamide), selumetinib (6-(4-bromo-2-chloroanilino)-7-fluoro-N-(2-hydroxyelhoxy)-3-methylbenzimidazole-5-carboxamide), PD-325901, Cl-1040, PD035901, tetrathiomolybtate, TAK-933, and the like and combinations thereof. In particular embodiments, the oncokinase inhibitor may be trametinib.

The oncokinase inhibitor can be provided in any amount capable of providing treatment. For example, the concentration of oncokinase inhibitor in the compositions of such embodiments can be up to about 30% (w/w), and in some embodiments, the concentration of oncokinase inhibitor may be up to about 20% (w/w). For example, in some embodiments, the composition may include about 0.1% (w/w) to about 30% (w/w), about 0.25% (w/w) to about 20% (w/w), about 0.5% (w/w) to about 15% (w/w), about 1% (w/w) to about 15% (w/w), about 1% (w/w) to about 10% (w/w), or any range or individual concentration of oncokinase inhibitor encompassed by these example ranges. In particular embodiments, the composition may include about 0.25% (w/w) to about 15% (w/w), about 0.5% (w/w) to about 10% (w/w), about 0.75% (w/w) to about 7.5% (w/w), about 1% (w/w) to about 5% (w/w), about 1% (w/w) to about 3% (w/w), or any range or individual concentration of encompassed by these example ranges.

The compositions of various embodiments may include a base such as, for example, white petrolatum, white petrolatum USP, mineral jelly, petroleum jelly, yellow petrolatum, yellow soft paraffin, white soft paraffin, fats, waxes, sterols, fat-soluble vitamins, monoglycerides, diglycerides, triglycerides, phospholipids, PCCA plasticized base, and the like and combinations thereof, and in certain embodiments, the base may be an emollient base.

In some embodiments, the base may be a liposomal base. Liposomal bases are an emulsion that includes a lipophilic component and an aqueous component that can be in the form of a lotion, a cream, a gel, or a paste. Examples of suitable liposomal bases include PCCA Lipoderm®, Lipoderm ActiveMax™, Anhydrous Lipoderm, and Lipoderm High Molecular Weight™ PCCA. Such liposomal base formulations can include, for example, about 60-80% wt/wt water combined with glycerin, $C_{12-15}$ alkyl benzoate, glyceryl stearate, dimethicone, cetearyl alcohol, cetearyl glucoside, polyacrylamide, cetyl alcohol, magnesium aluminum silicate, xanthan gum, aloe vera (aloe barbadensis), tocopheryl acetate (vitamin E acetate), prunus amygadalus amara (bitter almond) kernel oil, Vitis vinifera (Grape) seed extract, Triticum vulgare (wheat) germ oil, retinyl palmitate (vitamin A palmitate), ascorbyl palmitate (vitamin C palmitate), Pro-Lipo Multi-emulsion Liposomic System, tetrasodium EDTA, phenoxyethanol, sodium hydroxymethylglycinate and the like and combinations thereof.

In some embodiments, the base may be cream base. Cream bases are semi-solid emulsions of oil and water. They are divided into two types: oil-in-water (O/W) creams which are composed of small droplets of oil dispersed in a continuous water phase, and water-in-oil (W/O) creams which are composed of small droplets of water dispersed in a continuous oily phase. Oil-in-water creams are more comfortable and cosmetically acceptable as they are less greasy and more easily washed off using water. Water-in-oil creams are more difficult to handle but many drugs which are incorporated into creams are hydrophobic and will be released more readily from a water-in-oil cream than an oil-in-water cream. Water-in-oil creams are also more moisturising as they provide an oily barrier which reduces water loss from the stratum corneum, the outermost layer of the skin. Cream bases typically include water, oil, emulsifier, and thickening agents, such as those discussed below.

In some embodiments, the base may be a moisturizing cream base. Moisturizing cream bases are composed of the same components as the cream bases described above with the addition of an emollient or humectant, that may provide a barrier that reduces water loss from the stratum corneum, the outermost layer of the skin. The emollient or humectant in a moisturizing cream base may be cetyl esters wax, stearyl alcohol, cetyl alcohol, and glycerin, or combinations thereof. Example cream bases and moisturizing cream bases include VersaBase (PCCA); Emollient cream, Vanishing cream, CeraVe, Vanicream, Vitamin E; Cliniderm; Dermabase (purified water, petrolatum, mineral oil, cetostearyl alcohol); Eucerin (water, petrolatum, mineral oil, ceresin, lanolin alcohol, methylchloroisothiozolinone, methylisothiazolinone); Glaxal (WellSpring Pharmaceutical Corp., Sarasota, Fla.); stearic acid cream, or any other pharmaceutical cream base used for topical formulations known to those skilled in the art.

In some embodiments, the base may be an ointment base. Ointments are compositions in which oil and water are provided in a ratio of from 7:1 to 2:1, from 5:1 to 3:1, or 4:1, and in some embodiments, the ointment may or may not include water, such as Aquaphor, Pracasil, and plasticized bases. Ointments are generally formulated using oils, waxes, water, alcohols, petroleum products, silicones, water, and other agents to prepare formulations with various viscosities and solvent properties. Commonly used formulations include oleaginous base (White Ointment), absorption base, W/O emulsion base (Cold Cream type base), O/W emulsion base (Hydrophilic Ointment), water soluble base, in addition to others. These preparations are used to dissolve or suspend substances or products with medicinal or cosmetic value. In some embodiments, the base may be an emollient base. Non-limiting examples of emollient bases includes C9-C14 linear or branched alkyl alcohols, C3-C14 linear or branched polyols, C6-C14 di-esters of C6-C12 diacids, hydrocarbons, natural waxes, vegetable oils, and silicones, branched chain esters, ethoxylated partial glyceride fatty acid esters, protein derivatives, lanolin and lanolin derivatives, and fatty alcohol ethoxylates, emollient oils, fatty acids, fatty alcohols and their esters. such as, for example, isononyl isonanoate, dioctyl sebacate, isooctyl isooctanoate, dioctyl adipate, squalane, petrolatum, mineral oil, carnauba wax, candelilla wax, beeswax, sunflower oil, sesame oil, olive oil, cyclomethicone and dimethicone.

In some embodiments, the emollient base may be or may include polyols having the formula:

$$HOCH_2—[CHOH]_x—CH_2OH$$

wherein the index x is an integer from 1 to 20. In some embodiments, x is an integer from 1 to 10. Examples, of such polyols include glycerol, erythritol, xylitol, (2R,3R)-butane-1,2,3,4-tetrol, (2S,3R)-butane-1,2,3,4-tetraol, (2R,3S)-butane-1,2,3,4-tetraol, (2S,3S)-butane-1,2,3,4-tetrol, (2R,3R,4R)-pentane-1,2,3,4,5-pentol, (2S,3R,4R)-pentane-1,2,3,4,5-pentol, (2R,3S,4R)-pentane-1,2,3,4,5-pentol, (2R,3R,4S)-pentane-1,2,3,4,5-pentol, (2S,3S,4R)-pentane-1,2,3,4,5-pentol, (2S,3R,4S)-pentane-1,2,3,4,5-pentol, (2R,3S,4S)-pentane-1,2,3,4,5-pentol, and (2S,3S,4S)-pentane-1,2,3,4,5-pentol. In some embodiments, the emollient base may be glycerol.

The amount of base in the compositions of embodiments can vary and will depend on the amounts of the other components. More base can be added to compensate for smaller amounts of other components in the desired topical pharmaceutical formulation. In some embodiments, the base may be present in a concentration of about 45% (w/w) to about 99.75% (w/w) of the total composition, or any range or individual concentration known in the art.

In some embodiments, the compositions may further include a solubility enhancer. Without wishing to be bound by theory, oncokinase inhibitors including those described above may be insoluble in the bases described above. Thus, a solubility enhancer may be necessary to produce a topical composition that effectively delivers the oncokinase inhibitor to affected tissues. The solubility enhancers are not limited and may include various known solubility enhancers and combinations thereof. In particular embodiments, the solubility enhancer may be, for example, ethyl acetate, ethanol, methanol, dimethylformamide (DMF), acetone, acetonitrile, tetrahydrofuran (THF), acetic acid, dimethyl sulfoxide (DMSO), chloroform, propylene glycol, polyethylene glycol, propane-1,3-dioland the like and combinations thereof, and in some embodiments, the solubility enhancer may be DMSO. The composition may include about 10% (w/w) to about 40% (w/w) solubility enhancer, and in some embodiments, the composition may include at least about 25% (w/w) to about 35% (w/w) solubility enhancer.

The compositions of various embodiments can be in any forms, including, for example, liquid, creams, lotions, foams, liniments, and the like.

In some embodiments, the compositions described above may be formulated as a liquid. Liquid dosage forms for topical administration may include diluents such as, for example, alcohols, glycols, oils, water, and the like. Such compositions may also include wetting agents or emulsifiers. In some embodiments, the compositions of embodiments may be formulated as oil-in-water or water-in-oil emulsion. A cream can be a water-in-oil (w/o) emulsion in which an aqueous phase is dispersed in an oil phase, or an oil-in-water (o/w) emulsion in which an oil is dispersed within an aqueous base. An ointment generally refers to a more viscous oil-in-water cream. Traditional ointment bases (i.e. carrier) include hydrocarbons (petrolatum, beeswax, etc.) vegetable oils, fatty alcohols (cholesterol, lanoilin, wool alcohol, stearyl alcohol, etc.) or silicones. Insoluble solids such as starch, zinc oxide, calcium carbonate, or talc can also be used in ointments and creams. Gel forms of the compositions described above can be formed by the entrapment of large amounts of aqueous or aqueous-alcoholic liquids in a network of polymers or of colloidal solid particles. Such polymers or colloids (gelling or thickening agents) are typically present at concentrations of less than 10% w/w and include carboxymethyl cellulose, hydroxypropylmethyl cellulose, hydroxyethyl cellulose, methyl cellulose, sodium alginate, alginic acid, pectin, tragacanth, carrageen, agar, clays, aluminum silicate, carbomers, and the like.

In some embodiments, the compositions described above may further include one or more pharmaceutically acceptable diluents, fillers, disintegrants, binders, lubricants, surfactants, hydrophobic vehicles, water soluble vehicles, emulsifiers, buffers, humectants, moisturizers, solubilizers, preservatives, colorants, plastizers, carriers, excipients, and the like and combinations thereof. The person of ordinary skill in the art can refer to various pharmacologic references such as, for example, Modern Pharmaceutics, Banker & Rhodes, Marcel Dekker, Inc. (1979) and Goodman & Gilman's The Pharmaceutical Basis of Therapeutics, 6th Edition, MacMillan Publishing Co, New York (1980) for guidance in determining the amount of such components in the compositions and formulations of embodiments.

In some embodiments, the topical formulations can be in the form of a lotion. Lotions are low- to medium-viscosity topical preparation. Most lotions are oil-in-water emulsions containing an emulsifier such as cetyl alcohol to prevent separation of these two phases. Lotions can include fragrances, glycerol, petroleum jelly, dyes, preservatives, proteins and stabilizing agents. In some embodiments, the topical formulations can be in the form of a foam. Pharmaceutical foams are pressurized dosage forms containing one or more active ingredients that, upon valve actuation, emit a fine dispersion of liquid and/or solid materials in a gaseous medium. Foam formulations are generally easier to apply, are less dense, and spread more easily than other topical dosage forms. Foams may be formulated in various ways to provide emollient or drying functions to the skin, depending on the formulation constituents. Accordingly, this delivery technology is a useful addition to the spectrum of formulations available for topical use. In some embodiments, the topical formulations can be in the form of a liniment. Liniments or balms are topical formulations that are of a similar viscosity to lotions and less viscous than an ointment or cream. Liniments are generally applied with friction by rubbing the liniment into the skin. Liniments typically are formulated from alcohol, acetone, or similar quickly evaporating solvents and may contain counterirritant aromatic chemical compounds such as methyl salicilate, benzoin resin, or capsaicin.

Emollient or lubricating vehicles that help hydrate the skin can also be used. Examples of suitable bases or vehicles for preparing hydrating compositions for use with human skin are petrolatum, petrolatum plus volatile silicones, lanolin, cold cream (USP), and hydrophilic ointment (USP).

Vitamins include, for example, vitamin D, vitamin K, vitamin B (including niacinamide, nicotinic acid, C1-18 nicotinic acid esters, and nicotinyl alcohol; B6 compounds, such as pyroxidine; and B5 compounds, such as panthenol, or "pro-B5"), vitamin A (including retinoids such as retinyl propionate, carotenoids, and other compounds), vitamin E (including tocopherol sorbate, tocopherol acetate, other esters of tocopherol), vitamin C (including ascorbyl esters of fatty acids, and ascorbic acid derivatives, for example, ascorbyl glucoside, magnesium ascorbyl phosphate, sodium ascorbyl phosphate, and ascorbyl sorbate), and all natural and/or synthetic analogs thereof, and combinations thereof. In various embodiments, the compositions may include about 0.0001 wt. % to about 50 wt. %, about 0.001 wt. % to about 10 wt. %, about 0.01 wt. % to about 5 wt. %, or about 0.1 wt. % to about 1 wt. %, or any individual concentration or range of each vitamin contained in the composition.

In some embodiments, the compositions may include an antioxidant. Such antioxidant may be, for example, butylated hydroxytoluene, ascorbic acid, ascorbic palmitate, butylated hydroxyanisole, 2,4,5-trihydroxybutyrophenone, 4-hydroxymethyl-2,6-di-tert-butylphenol, erythorbic acid, gum guaiac, propyl gallate, thiodipropionic acid, dilauryl thiodipropionate, tert-butylhydroquinone, tocopherol, and the like and pharmaceutically acceptable salt or ester thereof or combinations thereof. The antioxidant can be present in a concentration of about 0.01% (w/w) to about 1% (w/w) of the total composition or any individual concentration encompassed by this example range.

In some embodiments, the composition may include an emulsifying agent including, for example, various monoglycerides, diglycerides, triglycerides, and blends thereof at a concentration of about 3% (w/w) to about 10% (w/w) of the total composition. In some embodiments, the compositions may further include a humectant that provides soothing, smoothing, moisturizing, or protects the skin. The humectant is not limited and can be, for example, calamine, dodecylsulphate, sodium lauryl sulphate (SLS), a polyoxyethylene ester of polysorbitan, such as monooleate, monolaurate, monopalmitate, monostearate esters, esters of sorbitan, the polyoxyethylenes ethers, the sodium dioctylsulphosuccinate (DOSS), lecithin, and sodium docusate. The amount of humectant in such compositions may be about 0.01% (w/w) to 5% (w/w) of the total composition.

In some embodiments, the composition may further include an analgesic agent such as, for example, methyl salicylate, codeine, morphine, methadone, pethidine, buprenorphine, hydromorphine, levorphanol, oxycodone, fentanyl, a non-steroidal anti-inflammatory drug (NSAID), and the like and cobinations thereof. The amount of the analgesic agent such compositions may be about 0.01% (w/w) to 5% (w/w) of the total composition.

In some embodiments, the compositions may further include a topical debriding agent such as, for example, papain/urea, balsam peru/castor oil/trypsin, chlorophyllin copper complex/papain/urea, collagenase, and the like and combinations thereof. The amount of the debriding agent in such compositions may be about 0.01% (w/w) to 5% (w/w) of the total composition.

Other embodiments of the invention include methods for treating congenital epidermal, dermal hyperplasia, or vascular anomalies by administering any of the compositions described above. The methods of various embodiments may include the steps of administering a composition of the various embodiments described above to the location of congenital epidermal, dermal hyperplasia, or vascular anomalies of a subject in need of treatment. The step of administering can be carried out by various means. For example, administering can be accomplished by applying the composition to the skin of a subject, and in some embodiments, the skin may be massaged or rubbed to facilitate contacting affected area. In some embodiments, the step of administering can be carried out one, two, three, four, or more times per day, and administering can be carried out the prescribed number of times per day for one week to six months or until the symptoms are resolved. In some embodiments, improvement in one or more symptoms may be observed within about 7 days of treatment, and in certain embodiments, improvement in one or more symptoms may be observed within about 1, about 2, about 3, about 4, about 5, or about 6 days after initial treatment.

Further embodiments include methods for making topical compositions containing one or more oncokinase inhibitor. Such embodiments may generally include the step of dissolving the one or more oncokinase inhibitor in solubility enhancer or solvent to create a oncokinase inhibitor solution and combining the oncokinase inhibitor with a base. The oncokinase inhibitor may be any of the oncokinase inhibitors described above, and the base may be any of the bases described above used to create, for example, topical liquids, creams, lotions, foams, liniments, and the like. As discussed above, the solubility enhancer may be, for example, ethyl acetate, ethanol, methanol, dimethylformamide (DMF), acetone, acetonitrile, tetrahydrofuran (THF), acetic acid, dimethyl sulfoxide (DMSO), chloroform, propylene glycol, polyethylene glycol, propane-1,3-diol and the like and combinations thereof, and in some embodiments, the solubility enhancer may be DMSO.

In some embodiments, the base may be a cream base. Cream bases can be prepared separately by conventional techniques well known to those skilled in the art. Generally, a suitable process includes admixing the various ingredients of the cream in appropriate relative amounts in any order that is convenient and thereafter, if necessary, adjusting the pH to the final desired value. For example, the components of the base may be mixed together at a temperature of about 65° C. to about 75° C. until an emulsion has formed, and therapeutic agent may be added after cooling the emulsified cream base or during mixing.

As is known in the art, certain means for administering may require the use of particular components of the formulation. Such components are described above and can be appropriately incorporated into the compositions.

EXAMPLES

Although the present invention has been described in considerable detail with reference to certain preferred embodiments thereof, other versions are possible. Therefore, the spirit and scope of the appended claims should not be limited to the description and the preferred versions contained within this specification. Various aspects of the present invention will be illustrated with reference to the following non-limiting examples.

Example 1

An emollient cream is prepared for pediatric patients having nevus sebaceous syndrome. The cream is administered directly to the affected area. Example creams are provided in Table 1:

TABLE 1

|  | Example 1 | Example 2 |
| --- | --- | --- |
| Trametinib | 1% | 0.5% |
| DMSO | 50% | 25% |
| Emulsifix | 2% | 1% |
| Emollient Cream | 47% | 73.5% |

Example 2

A liposome base containing topical composition is prepared for pediatric patients having superficial vascular anomalies. The composition is administered directly to the affected area. Example topical compositions are provided in Table 2:

TABLE 1

|  | Example 1 | Example 2 |
| --- | --- | --- |
| Trametinib | 1% | 0.5% |
| DMSO | 50% | 25% |
| Emulsifix | 2% | 1% |
| Lipoderm (Liposome base) | 47% | 73.5% |

What is claimed is:

1. A topical composition comprising an oncokinase inhibitor, a solubility enhancer, and a base, wherein the oncokinase inhibitor is trametinib (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1    (2H)- yl}phenyl) acetamide) at about 1% (w/w) to about 3% (w/w) of the composition and the solubility enhancer is dimethyl sulfoxide (DMSO).

2. The composition of claim 1, wherein the solubility enhancer is about 10% (w/w) to about 40% (w/w) of the composition.

3. The composition of claim 1, wherein the base is selected from the group consisting of white petrolatum, white petrolatum USP, mineral jelly, petroleum jelly, yellow petrolatum, yellow soft paraffin, white soft paraffin, fats, waxes, sterols, fat-soluble vitamins, monoglycerides, diglycerides, triglycerides, phospholipids, POCA plasticized base, and combinations thereof.

4. The composition of claim 1, wherein the base is a cream base, an emollient base, or a liposomal base.

5. The composition of claim 1, wherein the composition is in the form of topical liquids, creams, lotions, foams, or liniments.

6. A method for treating vascular anomalies, nevus sebaceous syndrome, epidermal nevi, and neurofibromas, the method comprising administering to a patient in need of treatment a topical composition containing about 1% (w/w) to about 3% (w/w) of an oncokinase inhibitor, a solubility enhancer, and a base, wherein the solubility enhancer is dimethyl sulfoxide (DMSO) and the oncokinase inhibitor is trametinib (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1 (2H)-yl}phenyl) acetamide).

7. The method of claim 6, wherein administering comprises applying the composition to the skin of the patient.

8. The method of claim 6, further comprising readministering the composition.

9. The method of claim 6, wherein the patient has epidermal and/or sebaceous nevi.

10. The method of claim 6, wherein the patient has port-wine stains, capillary malformations, Sturge-Weber syndrome, Klippel-Trenaunay syndrome, venous malformation, or lymphatic malformations.

11. The method of claim 6, wherein the base is selected from the group consisting of white petrolatum, white petrolatum USP, mineral jelly, petroleum jelly, yellow petrolatum, yellow soft paraffin, white soft paraffin, fats, waxes, sterols, fat-soluble vitamins, monoglycerides, diglycerides, triglycerides, phospholipids, PCCA plasticized base, and combinations thereof.

12. The method of claim 6, wherein the base is a cream base, an emollient base, or a liposomal base.

13. The method of claim 6, wherein the composition is in the form of topical liquids, creams, lotions, foams, or liniments.

14. The method of claim 6, wherein the composition contains about 10% (w/w) to about 40% (w/w) of the solubility enhancer.

* * * * *